United States Patent [19]

Blackburn

[11] Patent Number: 4,528,197
[45] Date of Patent: Jul. 9, 1985

[54] CONTROLLED TRIGLYCERIDE NUTRITION FOR HYPERCATABOLIC MAMMALS

[75] Inventor: George L. Blackburn, Cambridge, Mass.

[73] Assignee: KabiVitrum AB, Stockholm, Sweden

[21] Appl. No.: 461,077

[22] Filed: Jan. 26, 1983

[51] Int. Cl.³ .............................................. A01N 37/02
[52] U.S. Cl. ..................................................... 514/552
[58] Field of Search ......................................... 424/312

[56] References Cited

U.S. PATENT DOCUMENTS

| | | | |
|---|---|---|---|
| 4,272,548 | 6/1981 | Gatzen et al. | 424/312 |
| 4,330,557 | 5/1982 | Cavazza | 424/316 |
| 4,401,657 | 8/1983 | Kashiwabara et al. | 424/177 |
| 4,414,238 | 11/1983 | Schmidt | 424/654 |

OTHER PUBLICATIONS

V. K. Babayan, "Medium Chain Length Fatty Acid Esters and Their Medical and Nutritional Applications", JAOCS, Jan., 1981, pp. 49A–51A.

Primary Examiner—Elbert L. Roberts
Attorney, Agent, or Firm—Pollock, Vande Sande & Priddy

[57] ABSTRACT

Method and composition for enhancing protein anabolism in an hypercatabolic mammal. The method comprises parenterally administering to the mammal nutritionally sufficient sources for amino acids, carbohydrates and lipids, the lipids comprising a controlled triglyceride source which, on hydrolysis, yields both long chain fatty acids and medium chain fatty acids, preferably about 20 to 80% long chain fatty acids and about 80 to 20% medium chain fatty acids. In one embodiment, the composition has the additional benefit of being capable of providing more than 60% of the total caloric requirements of the mammal via the lipid source without immunological impairment of the reticuloendothelial system of the mammal.

11 Claims, 2 Drawing Figures

CONTROLLED TRIGLYCERIDE NUTRITION FOR HYPERCATABOLIC MAMMALS

BACKGROUND OF THE INVENTION

1. Field:

This disclosure is concerned generally with intravenous nutrition and specifically with the use of lipid combinations which, on hydrolysis, yield controlled amounts of both long and medium chain fatty acids.

2. Prior Art:

Among the most important goals of nutritional support during severe injury or sepsis are a reduction in net protein catabolism and an increase in protein synthesis, especially in those tissues concerned with wound healing and host defense mechanisms.

Usually during severe stress, regardless of the initiating cause, there is an important mobilization of amino nitrogen from skeletal muscle and connective tissue to support the synthesis of visceral and acute phase secretory proteins. This metabolic response results in the acceleration of protein degradation and an elevation of energy expenditure or, as used herein, hypercatabolism. In addition, muscle protein catabolism provides the precursors for oxidation of branched chain amino acids and the synthesis and release of alanine for hepatic metabolism as a gluconeogenic substrate. Urinary nitrogen excretion is often elevated and the organism suffers negative nitrogen balance. If the stress is persistent, the nitrogen losses will eventually deplete the body's protein pool and this hypercatabolism will compromise critical functions resulting in a progressive deterioration of lean body mass and multiple organ failure. There is no doubt about the importance of dietary amino acid administration during severe injury. But because of the close relationship between protein and energy metabolism, caloried intake can also modify the utilization of amino acids, spare nitrogen and support protein synthesis.

The sources of non-protein calories commonly used in total parenteral nutrition are dextrose solutions and long chain fatty acid triglyceride (LCT) emulsions composed of either soybean or safflower oil. However, there is increasing concern about the undesirable effects of excessive dextrose administration in critically ill patients. Insulin resistance limits glucose oxidation and promotes lipid biosynthesis increasing the production of $CO_2$ and the risks of developing fatty liver. On the other hand some controversy persists concerning the utilization of long chain fatty acids during severe stress. Some investigators have suggested that the nitrogen sparing capacity of long chain triglyceride emulsions are due solely to the glycerol that the emulsions contain. In severe stress long chain fatty acids may have a reduced capacity to enter the mitochondria for $\beta$-oxidation, some investigators have reported a reduction in muscle carnitine levels which assists their entry into the mitochondria.

In addition, intravenous diets in which long chain triglyceride emulsions contribute over 50% of nonprotein calorie intake have been associated with anergy to cutaneous antigens and T-lymphocyte dysfunction. Furthermore, critically ill patients receiving such diets are at increased risk of developing secondary complications.

These considerations have promoted the search for nonconventional energy sources that can be more easily utilized in injury. Medium chain triglycerides (MCT) formed from saturated fatty acid with chain lengths of 6-14 carbons have a unique metabolism that may be of importance during injury. They are metabolized more rapidly than long chain triglycerides because they do not require carnitine to enter into the mitochondria where they are used for $\beta$-oxidation. Moreover, the deposition as fat is less during medium chain triglyceride infusions than during long chain triglyceride administration because they require an initial elongation to 16-18 carbon length chains. Their rapid utilization as an energy substrate and frequent generation of ketone bodies may represent an important mechanism to spare nitrogen and support protein synthesis during injury. Proposed enteral and parenteral applications for MCTs have been described by A. C. Bach and V. K. Babayan in "Medium-Chain Triglycerides: an Update", Am. J. Clin. Nutrition 36, pp. 950-962, November, 1982. Parenteral applicatons of MCT/LCT mixtures have been described by D. Sailer and M. Müller in "Medium Chain Triglycerides in Parenteral Nutrition", J. Parent. and Ent. Nutr., Vol. 5, No. 2, pp. 115-119 (1981). Toxicity to intravenous administration of large quantities of MCT has been reported. Intravenous administration in dogs has produced somnolence, vomiting, coma and death. Similar findings have also been observed in fed, but not fasted rats. The effects of such nutrition on the hypercatabolic mammal, however, have not been investigated in great detail to date. As used herein, the term hypercatabolic refers to a state of elevated energy expenditure in a mammal which, if uncorrected, results in detrimental protein catabolism. Such state may be caused by a variety of life-threatening conditions including surgical injury, trauma, infection and the like.

As disclosed below, we have examined various calorie sources for total parenteral nutrition (TPN) in burned rats. We have examined the significance of infusing in addition to a basal intake of dextrose and amino acids, 33% more calories as either dextrose or a commercially available long chain triglyceride emulsion (soybean oil), medium chain triglyceride emulsion or a structured lipid emulsion composed of 60% medium chain and 40% long chain triglycerides. We evaluated the effect of these diets on changes in body weight, nitrogen balance, lever nitrogen, serum glucose, $\beta$-hydroxybutyrate, lactate and albumin concentrations. Whole body leucine kinetics and protein fractional synthetic rate in muscle and liver were determined by using a constant intravenous infusion of L-[1-$^{14}$C]leucine as a tracer. Quite surprisingly, we found that when certain lipid sources were included in the TPN studies, the mammals studies were significantly more anabolic than animals receiving the other intravenous diets. As measured by nitrogen and net leucine balance, rats infused with one of our controlled lipid sources were in significant positive balance. Using the same controlled lipid, the highest hepatic protein synthesis was obtained and, in addition, it was found that more than 60% of the test animals' total caloric requirements could be satisfied with that lipid source without impairment of the function of the animal's reticuloendothelial system (RES). Details of the controlled lipid sources and their uses are described below.

SUMMARY OF THE INVENTION

We have found that it is possible to enhance protein anabolism in an hypercatabolic mammal by parenterally administering to the mammal nutritionally sufficient sources for amino acids, carbohydrates and lipids, the lipids themselves comprising a controlled source of triglycerides which, on hydrolysis, yields both long chain fatty acids and medium chain fatty acids, preferably about 20 to 80% long chain fatty acids and about 80 to 20% medium chain fatty acids. The controlled source of triglycerides is capable of providing more than 60% of the hypercatabolic mammal's caloric requirements without impairment of the RES of the mammal. In one embodiment the lipids comprise a mixture of synthetic triglycerides (or structured lipids) having the formula

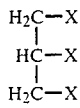

$$\begin{array}{c} H_2C-X \\ | \\ HC-X \\ | \\ H_2C-X \end{array}$$

where X represents long and medium chain fatty acid residues with at least one of each being present. Preferably, a long chain fatty acid residue is an essential fatty acid residue and a medium chain fatty acid residue is selected from the group consisting of $C_8$, $C_{10}$, and $C_{12}$ saturated fatty acid residues. In another embodiment, the lipids comprise a physical mixture of long chain triglycerides and medium chain triglycerides.

SPECIFIC EMBODIMENTS

Material and Methods

Animals and Experimental Design

Male Spraque-Dawley rats (Charles River Breeding Laboratories, Wilmington, MA) were maintained in individual cages in a light-controlled room at a temperature of 26°–28° C. During one week prior to study they were fed a stock laboratory diet (Charles River D-3000, Agway Agricultural Products, Minneapolis, MN) and tap water and libitum. After that period, under sodium pentobarbital anesthesis (25 mg/kg body wt), 35 rats weighing between 215–265 g underwent insertion of a 0.020″ × 0.037″ Silastic ® catheter (Dow Corning Labs., Corning, NY) through the external jugular vein into the superior vena cava as has been described. The catheter was attached to a flow-through swivel (Instech Lab., Philadelphia, Pa.) that allowed a continuous infusion and free movement by the rats. At the same time the animals received a full thickness scalk burn injury by immersing 25% of their body surface area in boiling water for 15 seconds. Following one day of recovery with intravenous infusion of 0.9% sodium chloride the rats were randomly assigned to five groups of seven animals each to receive total parenteral nutrition using a Holter peristaltic pump (Holter #903, Extracorporeal Co., King of Prussia, PA) for three days. All animals received isovolemic solutions (31 ml/100 g body weight) containing 3.68% amino acids (Aminosyn, Abbott Laboratories, North Chicago, ILL), 14.6% dextrose, electrolytes, trace elements and vitamins that delivered 11.4 g amino acid/kg BW.day and 200 kcals/kg BW.day (Table 1).

TABLE 1

| Electrolyte, Trace Element and Vitamin Content of the Total Parenteral Nutrition Solutions | |
|---|---|
| Electrolytes | (g/liter) |
| Sodium Chloride | 1.19 |
| Sodium acetate | 1.67 |
| Potassium chloride | 1.52 |
| Potassium phosphate | 1.06 |
| Potassium acetate | 1.00 |
| Magnesium sulfate | 0.99 |
| Calcium gluconate | 1.25 |
| Trace Elements | (mg/liter) |
| Chromium chloride ($CrCl_3.6H_2O$) | 0.2 |
| Zinc chloride | 21.2 |
| Cupric chloride ($CuCl_2.2H_2O$) | 9.1 |
| Mangenese chloride ($MnCl_2\ 4H_2O$) | 4.9 |
| Sodium iodide | 0.2 |
| Vitamins | (per liter) |
| Ascorbic acid | 68 mg |
| Retinol | 2230 IU |
| Ergocalciferol | 135 IU |
| Thiamine | 2.0 mg |
| Riboflavin | 2.4 mg |
| Pyridoxine | 2.7 mg |
| Niacin (as an amide) | 27.1 mg |
| Dexapanthenol | 10.2 mg |
| Di-alphatocopherol | 10.2 mg |
| Biotin | 40.6 ug |
| Folate | 0.3 mg |
| Cyanocobalamin | 3.4 ug |
| Choline chloride | 203 mg |

To Group I no additional calories were given. Groups II, III, IV and V received an additional 100 calories/kg BW.day as either dextrose (Group II); a soybean oil lipid emulsion (Intralipid ®), (Group III); a medium chain triglyceride emulsion composed of 75% capric acid (C8:0) and 25% caprylic acid (C10:0) (oil obtained from Captial City Products, Columbus, OH) (Group IV); or a chemically structured lipid emulsion composed of triglycerides synthesized from 40% safflower oil and 60% medium chain triglycerides (Captex 810 B, Capital City Products). The Captex 810 B product is a synthetic fat also referred to as a structured lipid. The preparation and use of such structured lipids is described in U.S. Pat. No. 3,450,819 to V. Babayan et al., incorporated herein by reference. All of the lipid emulsions were provided by Cutter Laboratories, Berkeley, CA. The composition of the administered nutrients is presented in Table 2.

TABLE 2

| | Dietary Intake in the Experimental Groups | | | | |
|---|---|---|---|---|---|
| | Total Calorie Intake (kcal/kg · day) | Protein Intake (gAA/kg · d) | Calorie:N Ratio | Nonprotein Calories | |
| | | | | % Dextrose | % Lipid |
| Group I (AA + low Dextrose) | 200 | 11.4 | 110:1 | 100 | 0 |
| Group II (AA + high Dextrose) | 300 | 11.4 | 165:1 | 100 | 0 |
| Group III (AA. Dextrose + LCT emulsion) | 300 | 11.4 | 165:1 | 65 | 35 |
| Group IV (AA. Dextrose + MCT emulsion) | 300 | 11.4 | 165:1 | 65 | 35 |
| Group V (AA. Dextrose + Structured Lipid) | 300 | 11.4 | 165:1 | 65 | 35 |

The animals were reweighed at the beginning and after three days of total parenteral nutrition. Total urinary excretion was collected daily.

During the last 3.5 hours of parenteral nutrition support, the rats were housed in closed metabolic chambers that allowed the collection of the expired breath. At this time, a tracer amount of L-[1-$^{14}$C]leucine (New England Nuclear Laboratories, Boston, MA) was added to nutrient solutions so that 1 $\mu$Ci/hour was infused. [$^{14}$C] Radioactivity in the expired breath and total carbon dioxide production were measured hourly. At the end of the isotope infusion, the rats were killed by decapitation and arterial-venous blood from the neck was drained into chilled empty and hepaninized tubes. The blood samples were centrifuged and 0.5 ml of serum was deproteinized with equal amounts of 30% perchloric acid for glucose, $\beta$-hydroxybutyrate and lactate measurements. Immediately after the blood collection the whole liver was weighed, a sample was stored in normal saline solutions for nitrogen analysis and a piece of gastrocnemius muscle was homogenized in 5 ml of ice-cold 10% sulphosalicylic acid and stored at $-30°$ C.

Analytical Methods

Daily nitrogen balances were calculated based on the total urinary nitrogen excretion. Total urine nitrogen as well as total liver nitrogen were determined using spectrophotometric analysis (Autoanalyzer, Technicon Instrument Co., Tarryton. NY) following a micro-Kjeldahl digestion (Technicon Block Digestor). Glucose, $\beta$-hydroxybutyrate and lactate levels were determined on the deproteinized serum by enzymatic methods. Serum insulin was determined by a double isotope radioimmunoassay and serum albumin by bromocresol green colorimetry.

During the constant infusion of L-[1-$^{14}$C]leucine, room air was circulated through the chambers at a rate of 1.6 L/min and the [$^{14}$C] labeled carbon dioxide appearance in the expired breath was trapped in scintillation vials containing hyamine hydroxide (Packard Instrument Co., Downers Grove, ILL) and measured with a Beckman LS-8000 liquid scintillation spectrometer (Beckman Instruments, Fullerton, CA) as described. The total $CO_2$ production was measured by trapping timed collections of expired breath in barium hydroxide (ASCARITE II ®, A. H. Thomas & Co., Philadelphia, Pa.).

Plasma amino acid concentrations were determined on the supernatant of 1 ml of plasma treated with 0.2 ml of 30% sulphosalicylic acid and separated by centrifugation using a D-400 Amino Acid Analyzer (Dionex Corporation, Sunnyvale, Calif.). Free leucine specific radioactivity was determined as previously described. Plasma ketoisocaproate (KIC) was eluted off a $C_{18}$-reverse phase 10u Bondapak column (Waters Associates, Medfield, Massi) using a 95% phosphate buffer, 5% acetonitrile solution at 0.9 mls/min. The KIC was detected at 210 nm and the peaks were manually collected for liquid scintillation spectrometry.

Total [$^{14}$C] radioactivity of plasma and infusate was measured using a commercial scintillant (Monofluor, National Diagnostic Inc., Somervile, N.J.). Efficiency of counting (between 65–75%) was calculated with external standards and all samples were counted to a standard error of less than 2.5%.

The muscle precipitates were washed 3 times with 2% sulphosalicylic acid and after being dried they were solubilized in quaternary ammonium hydroxide (Soluene-350, Packard Co.) to be counted in a commercial scintillant (Betafluor; National Diagnostic Inc., Sommerville, N.J.) and spectrophotometrically analyzed for total nitrogen following micro-Kjeldahl digestion.

Calculations

Rates of whole body leucine appearance have been estimated from the equation:

$$Q = I/Sp \text{ max}$$

where Q (Flux) is the amount of leucine entering and leaving the plasma pool in $\mu$mol.h$^{-1}$; I is the isotopic intravenous infusion rate in dpm.h$^{-1}$; and Sp max is the specific radioactivity of plasm free L-leucine at the end of the 3.5 h infusion. It was assumed a plateau labeling (steady state) of the plasma compartment was achieved when it was reached in the expired breath (between 2–3.5 h of continuous L-[1-$^{14}$C]leucine infusion).

The percentage of flux oxidized was derived from the [$^{14}$C]carbon dioxide in the expired breath (estimating that 10% did not appear in the breath) in dpm, the hourly production of $CO_2$ and the known infusion rate of the tracer (I). The oxidation rate of leucine was then calculated by multiplying the flux (Q) by the percentage oxidized.

The incorporation of leucine into whole body protein was subsequently derived from the difference between leucine flux and oxidation and the leucine release from protein breakdown from the difference between flux and intake. The leucine intake as a component of the nutrient solution was the same in all the animals.

The fractional muscle protein synthetic rate was derived from the equation of Garlick et al.

$$SB/Si = \frac{\lambda i}{(\lambda i - ks)} \cdot \frac{(1 - e^{-ks \cdot t})}{(1 - e^{-\lambda i \cdot t})} - \frac{ks}{(\lambda i - ks)}$$

where SB is the specific radioactivity of leucine in the sulphosalicylic precipitated proteins and Si is the specific radioactivity of plasma ketoisocaproate obtained at the end of the infusion, both in dpm/$\mu$mol; $\lambda i$ is the rate constant for the rise in specific radioactivity of the precursor in days$^{-1}$; and $K_s$ was the fraction of protein mass renewed each day in %/day. Because ketoisocaproate is generated in skeletal muscle from the deamination of leucine, its specific radioactivity represents the specific radioactivity of leucine in the muscle intracellular pool where leucine is transaminated.

Statistical Analysis data is presented as means $\pm$ SEM for each group of 7 rats and were analyzed using an IBM 370/CMS-VSI computer system with the BMDP statistical package (Regents of the University of California, Los Angeles, Calif.). The groups of animals were compared by one-way analysis of variance and student's t test (two-tailed). Student's t test among the different groups was performed only when ANOVA test reached a 95% confidence level.

Results

The body weights before nutrient administration and the calories and amino acid intakes during the study period are summarized in Table 3.

TABLE 3

Initial Body Weight and Actual Dietary Intake During Feedings

| GROUP Treatment: Base Solution + additional calories as: | I — | II Dextrose | III LCT | IV MCT | V Structured Lipid |
|---|---|---|---|---|---|
| N | 7 | 7 | 7 | 7 | 7 |
| Body Weight, g (Initial) | 246 ± 4 | 246 ± 7 | 238 ± 5 | 245 ± 4 | 238 ± 4 |
| Pre-TPN Body Weight, g | 238 ± 5 | 238 ± 5 | 233 ± 6 | 240 ± 6 | 231 ± 6 |
| Actual Calorie Intake, kcals/kg · day | 192 ± 4 | 292 ± 7** | 290 ± 8** | 281 ± 4** | 306 ± 7** |
| Nitrogen Intake g/kg · day | 1.74 ± 0.04 | 1.77 ± .04 | 1.75 ± 0.05 | 1.70 ± 0.03 | 1.86 ± 0.04 |

Data expressed as mean ± SEM:
**p < 0.01 vs group I

There was no difference in body weight among the five groups at the time of venous cannulation and one day following burn injury when maintained with only saline solutions.

FIG. 1 shows the percentage of body weight change after three days of different nutritional support. The animals which received additional calories as dextrose, soybean oil emulsion or structured lipid emulsion gained weight significantly, whereas those receiving medium chain triglyceride emulsions (IV) lost weight similar to the hypocaloric feeding group (I).

The cumulative nitrogen balance during the parenteral infusion (FIG. 2) did not show statistical differences among the groups. However, only those animals which received the additional 100 kcals/kg BW·day were in positive nitrogen balance and in rats given the structured lipid emulsion, the balance was significantly positive (p<0.05).

Serum glucose, β-hydroxybutyrate and insulin levels (Table 4) were different in rats given various diets. The lipid emulsions increased serum glucose and β-hydroxybutyrate concentrations compared with animals which received all of their nonprotein calories as dextrose. Serum insulin levels were clearly higher in those rats with increased dextrose intake (II) as well as animals given the medium chain triglyceride emulsion (IV).

TABLE 4

Serum Substrates and Insulin Concentrations

| GROUP TPN + additional calories as: | I — | II Dextrose | III LCT | IV MCT | V Structured Lipid |
|---|---|---|---|---|---|
| Glucose (mg/dL) | 121.0 ± 4.0 | 121.0 ± 7.2 | 180.6* ± 22.2 | 147.3 ± 15.7 | 161.3** ± 12.6 |
| β-Hydroxybutyrate (mmol/L) | 0.075 ± 0.02 | 0.051 ± 0.01 | 0.101^I ± 0.02 | 0.257*^I ± 0.08 | 0.123^I ± 0.03 |
| Lactate (mmol/L) | 4.52 ± 0.51 | 4.48 ± 0.30 | 4.60 ± 0.31 | 4.49 ± 0.49 | 4.30 ± 0.34 |
| Insulin (μU/ml) | 22.6 ± 2.2 | 31.6** ± 1.6 | 21.3 ± 2.5 | 29.5 ± 2.5 | 22.6 ± 1.5 |

Data expressed as mean ± SEM;
**p < 0.05 and
**p < 0.01 vs group I (Student's t test)
^I p < 0.05 versus group II (Student's t test)

Liver weight and the percentage of protein were similar among the five groups (Table 5).

TABLE 5

Liver Protein Content and Serum Albumin Concentrations

| GROUP TPN + additional calories as: | I — | II Dextrose | III LCT | IV MCT | V Structured Lipid |
|---|---|---|---|---|---|
| Liver weight (g/kg BW) | 42.3 ± 2.3 | 48.3 ± 1.9 | 51.9 ± 3.7 | 50.2 ± 2.3 | 49.8 ± 3.5 |
| Liver % protein (%) | 16.2 ± 0.6 | 15.8 ± 0.3 | 15.7 ± 0.4 | 15.5 ± 0.2 | 16.5 ± 0.5 |
| Liver Nitrogen (g/kg BW) | 1.09 ± 0.04 | 1.21* ± 0.04 | 1.29* ± 0.07 | 1.22 ± 0.05 | 1.30* ± 0.06 |
| Serum Albumin (g/dl) | 2.94 ± 0.11 | 3.17 ± 0.09 | 3.11 ± 0.26 | 3.40** ± 0.07 | 4.06** ± 0.17 |

Data expressed as mean ± SEM;
**p < 0.05 and
**p < 0.01 vs group I (Student's t test)

Nevertheless, rats receiving additional dextrose, soybean oil or structured lipid emulsions showed increased nitrogen content in the liver. Serum albumin was markably better in the groups infused with medium chain triglycerides (IV, V). The group with the structured lipid emulsion presented an albumin concentration 38% higher than the hypocaloric fed group (I).

Plasma amino acid concentrations are given in Table 6. Again, the animals which received either the medium chain or structured lipid emulsions had a significant reduction in branched chain amino acids without changes in the total amino acid concentrations.

TABLE 6

Plasma Amino Acid Concentrations

| (nmol/L) | TAU | ASP | THR | SER | GLN | GLY | ALA | VAL | ISO | LEU | TYR | PHE | TAA | BCAA |
|---|---|---|---|---|---|---|---|---|---|---|---|---|---|---|
| Group I | 346 ± 21 | 114 ± 64 | 621 ± 56 | 490 ± 42 | 134 ± 3 | 1038 ± 162 | 942 ± 126 | 731 ± 30 | 290 ± 27 | 402 ± 35 | 46 ± 2 | 165 ± 16 | 5319 ± 445 | 1422 ± 93 |
| Group II | 419 ± 56 | 54 ± 5 | 770 ± 54 | 571 ± 37 | 130 ± 5 | 984 ± 61 | 990 ± 50 | 715 ± 22 | 269 ± 10 | 347 ± 10 | 37 ± 5 | 139 ± 5 | 5425 ± 209 | 1331 ± 37 |
| Group III | 299 ± 64 | 43 ± 6 | 749 ± 51 | 614* ± 32 | 96** ± 6 | 1125 ± 145 | 968 ± 98 | 624 ± 109 | 301 ± 38 | 389 ± 48 | 46 ± 8 | 17♣ ± 16 | 5458 ± 534 | 1314 ± 181 |
| Group IV | 379 ± 58 | 50 ± 6 | 616 ± 51 | 482 ± 29 | 80 ± 2 | 824 ± 83 | 968 ± 35 | 550** ± 38 | 205* ± 16 | 286** ± 16 | 38 ± 3 | 152 ± 8 | 4632 ± 266 | 1042** ± 70 |
| Group V | 501 ± 50 | 43 ± 5 | 757 ± 40 | 661** ± 30 | 114 ± 11 | 1229 ± 139 | 890 ± 51 | 478** ± 26 | 174** ± 8 | 216** ± 13 | 37 ± 6 | 147 ± 6 | 5245 ± 179 | 870** ± 45 |

*p < 0.05 vs Group I
**p < 0.01 vs Group I
TAU = taurine, ASP = aspartate, THR = threonine, SER = serine, GLN = glutamine, GLY = glycine, ALA = alanine, VAL = valine, ISO = isoleucine, LEU = leucine, TYR = tyrosine, PHE = phenylalanine, TAA = total amino acids, BCAA = branched chain amino acids The changes in leucine kinetics are summarized in Table 7. During a constant amino acid infusion administering leucine at 62.2±0.65 μmols/100 g body weight·h, whole body leucine appearance, incorporation into and release from protein did not show major changes. However, leucine oxidation was significantly reduced in the rats which received additional calories as a structured lipid emulsion (V). This group also was the only one that showed an improvement in net leucine balance (difference between incorporation into and release from protein) compared with the control group (I).

Protein fractional synthetic rate in the gastrocnemius muscle (Table 7) changed only minimally with the addition of dextrose or different lipid emulsions over the hypocaloric parenteral feeding in these burned rats.

TABLE 7
Whole Body Leucine Kinetics and Muscle Protein Fractional Synthesis Rate (FSR)

|   | Flux | Oxidation | Incorporation Into Protein μ mols leucine/ 100/g BW · BW | Release from Protein | Balance | Muscle Protein FSR % day |
|---|---|---|---|---|---|---|
| I | 93.6 ± 7.7 | 30.0 ± 3.3 | 63.6 ± 5.0 | 29.3 ± 7.1 | +34.2 ± 3.2 | 8.4 ± 0.8 |
| II | 84.2 ± 3.8 | 22.5 ± 1.3 | 61.7 ± 3.8 | 22.1 ± 3.7 | +39.5 ± 1.8 | 10.3 ± 0.7 |
| III | 99.3 ± 6.8 | 23.6 ± 1.9 | 75.7 ± 5.8 | 37.8 ± 6.8 | +38.0 ± 1.9 | 8.9 ± 0.9 |
| IV | 83.0 ± 5.3 | 24.7 ± 7.3 | 58.3 ± 3.4 | 21.1 ± 4.9 | +37.2 ± 2.2 | 9.5 ± 0.8 |
| V | 81.7 ± 4.6 | 17.7** ± 1.2 | 64.1 ± 4.2 | 20.6 ± 4.7 | +43.5* ± 1.3 | 9.4 ± 0.5 |

Data expressed as mean ± SEM;
*p < 0.05 and
**p < 0.01 versus Group I (Student's t test)

Effects on RES (guinea pig studies)

Increased lipid rather than carbohydrate administration has been recommended for traumatized patients because it decreases $CO_2$ production, is isotonic, and does not stimulate hepatic lipogenesis. It is now evident that excessive intakes of carbohydrate increase carbon dioxide production and may lead to pulmonary dysfunction in compromised individuals. The associated hyperinsulin response to high carbohydrate intake has also been implicated as an indication of the Kwashiookor-like malnutrition which results in reduced hepatic secretory protein concentrations. However, results also suggest that high lipid administration may increase the risk of infections by impairing the animal's RES. The standard technique for producing fibronectin deficiency and reticuloendothelial system blockade in experimental animals is to administer long chain fatty acid triglyceride emulsions. Presently available IV fat emulsions caution against using the emulsions for more than 60% of the patient's total calories.

To evaluate the potential blocking of the RES during lipid administration, burned guinea pigs were parenterally fed isocaloric, isonitrogenous diets for three days in which 50% or 75% of the non-protein calories were administered as a long chain triglyceride (LCT), medium chain triglyceride emulsion (MCT) or the synthetic triglyceride (Captex 810 B) described above. The guinea pigs received a total of 300 Kcals/kg body weight·day, and 12.5 g amino acid/kg body weight·day for three days following a 25% full-thickness burn. The diets were intravenously administered through a central venous catheter and differed only in the source of lipid administered as well as the ratio of lipid to glucose non-protein calories. On the last day, the uptake of $^{59}$Fe-*Pseudomonas aeruginosa* by the RES was measured. $1 \times 10^6$ bacteria/gram of body weight were incubated for 48 hours with 50–100 μU of 59 Fe-citrate. The radiolabeled bacteria were washed and intravenously injected into the guinea pigs to produce an initial blood bacteremia of $1 \times 10^7$ c.f.u./ml of blood. After 60 minutes, the guinea pigs were exsanguinated and the quantity of radiolabeled bacteria sequestered on the organs of the reticuloendothelial system were determined. The results obtained comparing the LCT with the MCT are shown in Table 8. The results obtained comparing the LCT with the Captex 810 b are shown in Table 9.

TABLE 8
(LCT vs. MCT)

| (% Uptake) X ± S.D. | 50% Lipid | | | 75% Lipid | | |
|---|---|---|---|---|---|---|
|  | Unburned LCT | Burned LCT | Burned MCT | Unburned LCT | Burned LCT | Burned MCT |
| Liver | 46.5 ± 2.8 | 47.5 ± 4.6 | 44.0 ± 5.2 | 45.2 ± 7.7* | 28.0 ± 7.7* | 43.5 ± 6.2 |
| Lung | 1.9 ± 0.5 | 1.6 ± 0.2 | 2.0 ± 0.6 | 2.5 ± 0.9 | 6.8 ± 5.9* | 2.4 ± 0.7 |

*p < 0.05 vs MCT.

These results suggest that high Lipid administration as LCT following a thermal injury reduce the uptake of bacteria in the liver and increase localization of bacteria in the lungs. These defects are not seen when the source of Lipid is MCT. Previous studies with LCT in hypocaloric regimens have shown similar defects in the RES when only Lipid was administered. It can be concluded that RES function is dependent not solely on the quantity of Lipid administered but also the type of Lipid infused.

TABLE 9
(LCT vs. Synthetic triglyceride - [SYN.T.])

| (% Uptake) X ± S.D. | 50% Lipid | | | 75% Lipid | | |
|---|---|---|---|---|---|---|
|  | Unburned LCT | Burned LCT | Burned SYN.T. | Unburned LCT | Burned LCT | Burned SYN.T. |
| Liver | 46.5 ± 2.8 | 47.5 ± 4.6 | 44.0 ± 6.4 | 45.2 ± 5.2 | 28.0 ± 7.7* | 41.5 ± 3.9 |
| Lung | 1.9 ± 0.5 | 1.6 ± 0.2 | 2.0 ± 0.6 | 2.5 ± 0.9 | 6.8 ± 5.9* | 2.79 ± 1.4 |

*p < 0.05 vs MCT.

Although both the MCT and the SYN.T. (structured lipid) could be administered in amounts greater than 60% of the caloric requirements of the hypercatabolic guinea pigs, it was found that the use of the MCT at the 75% caloric level resulted in a significantly higher rate of complications and mortality than the SYN.T. given at the same 75% level, or the LCT or Dextroxe combinations in protein-depleted guinea pigs. These results are summarized in Table 10.

The studies were identical to those previously described except that the guinea pigs were protein-depleted by consuming a 2% casein diet for two weeks prior to the thermal injury.

TABLE 10

| Combination | # Animals | (Complications*/Mortality) Complications | Mortality |
|---|---|---|---|
| AA + LCT | 12 | 2 | 1 |
| AA + Dextrose | 13 | 4 | 0 |
| AA + MCT | 11 | 8 | 5 |
| AA + SYN.T. | 12 | 4 | 1 |

*MCT Complications:
Acute Renal Failure - 1
Pulmon/Cardiac Failure - 4
Rectal Prolapse - 2

Given the above disclosures, it is thought that numerous variations will occur to those skilled in the art. Accordingly, it is intended that the above examples should be construed as merely illustrative and that the inventions disclosed herein should be limited only by the following claims.

LEGENDS

Figure 1:
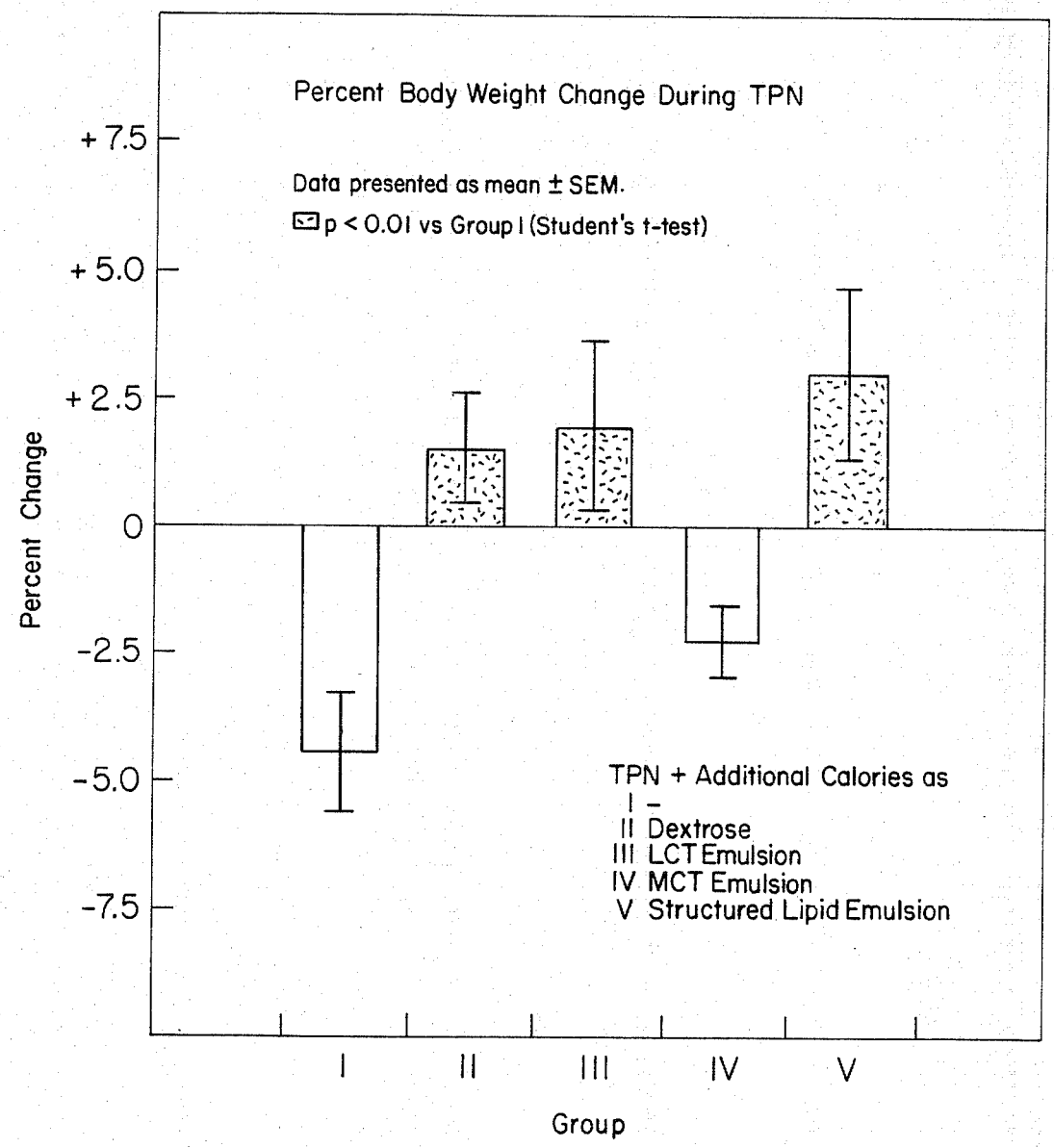
FIG. 1 is a graph comparing % body weight change with various I.V. nutritional supports disclosed herein.

FIG. 1—Changes in Body Weight Following a Burn in Rats Receiving Different Total Parenteral Nutrition Regimens.

Changes in body weight reflect the differences between the first day following the burn when the animal was only infused with saline and the end of the study at sacrifice.

Figure 2:
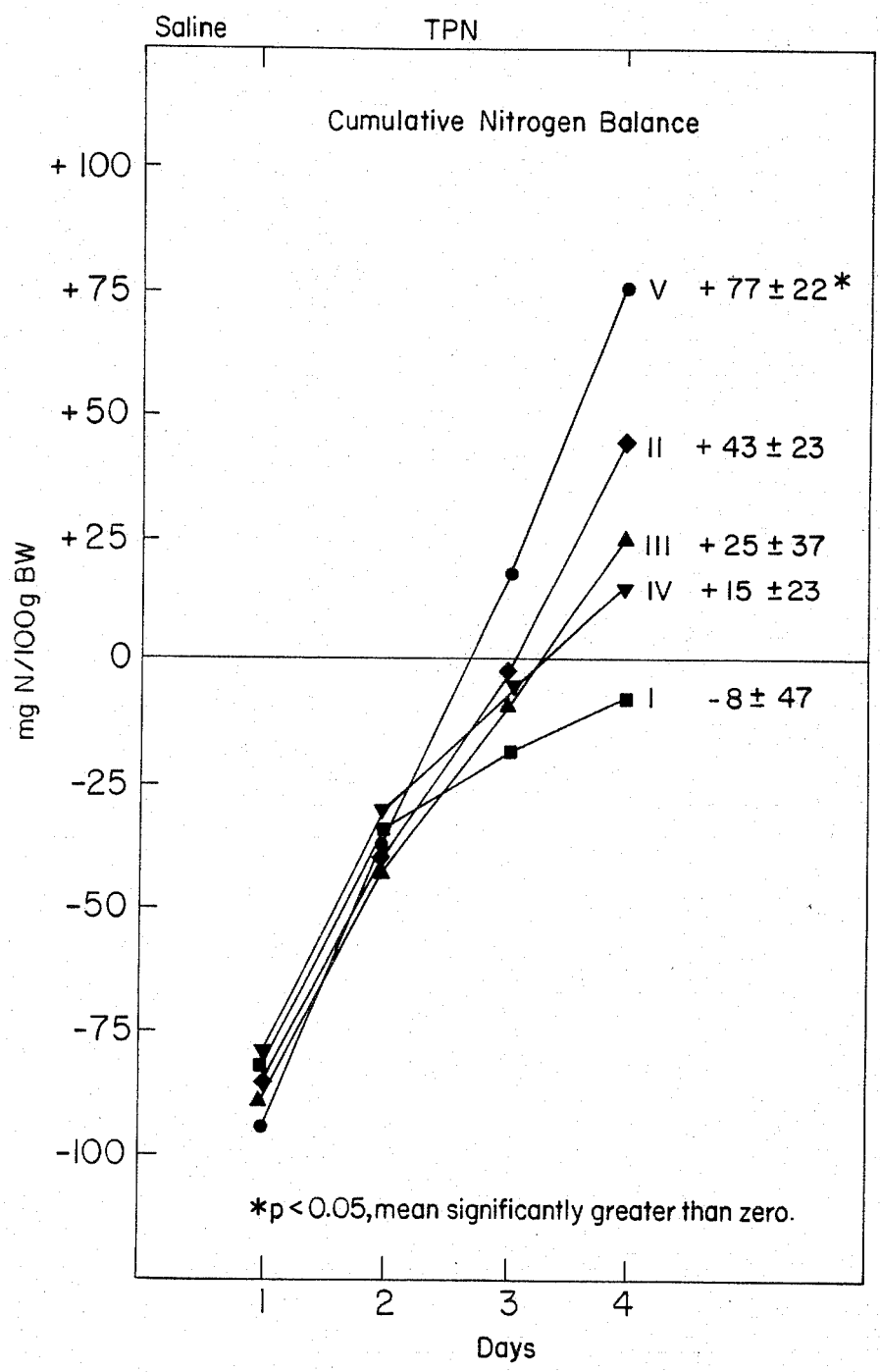
FIG. 2 is a graph showing cumulative nitrogen balance with the same various I.V. nutritional supports.

FIG. 2—Daily Cumulative Nitrogen Balance

During the first day following the burn injury all of the animals were infused with only physiologic saline. By the end of the fourth day, all of the animals receiving additional calories were in positive balance but only in rats given the structured lipid emulsion were the differences from zero statistically significant. Values represent the means and standard error for each group.

I claim:

1. A method of enhancing protein anabolism in a hypercatabolic mammal, the method comprising parenterally administering to the mammal nutritionally sufficient sources for carbohydrates, amino acids and lipids, the lipid source comprising an emulsion of triglycerides which, on hydrolysis, yields both long chain fatty acids and medium chain fatty acids.

2. The method of claim 1, wherein the total amount of lipids administered is capable of providing more than 60% of the total caloric requirements of the hypercatabolic mammal without impairment of the mammal's RES.

3. The method of claim 1 where in the lipids comprise a mixture of synthetic triglycerides having the formula

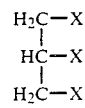

where X represents long and medium fatty acid residues with at least one of each being present.

4. The method of claim 3 where a long chain fatty acid residue is an essential fatty acid residue.

5. The method of claim 3 where a medium chain fatty acid residue selected from the group consisting of $C_8$, $C_{10}$ and $C_{12}$ fatty acid residues.

6. The method of claim 1 wherein the lipids comprise a physical mixture of long chain triglycerides and medium chain triglycerides.

7. A method capable of safely providing more than 60% of the caloric requirements of a hypercatabolic mammal via a lipid source without impairment of the mammal's RES, the method comprising parenterally administering to the mammal in combination with nutritionally acceptable amino acid and carbohydrate sources, an emulsion of triglycerides which, on hydrolysis, yields both long chain fatty acids and medium chain fatty acids.

8. The method of claim 7 wherein the lipids comprise a mixture of synthetic triglycerides having the formula

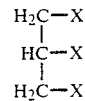

where X represents long and medium fatty acid residues, with at least one of each being present.

9. The method of claim 8 where a long chain fatty acid residue is an essential fatty acid residue.

10. The method of claim 8 where a medium chain fatty acid residue is selected from the group consisting of $C_8$, $C_{10}$ and $C_{12}$ fatty acid residues.

11. The method of claim 7 wherein the lipids comprise a physical mixture of long chain triglycerides and medium chain triglycerides.

* * * * *

UNITED STATES PATENT AND TRADEMARK OFFICE
CERTIFICATE OF CORRECTION

PATENT NO. : 4,528,197
DATED : July 9, 1985
INVENTOR(S) : George L. Blackburn

It is certified that error appears in the above—identified patent and that said Letters Patent is hereby corrected as shown below:

Column 1, line 37, change "caloried" to --- caloric ---.
Column 2, line 45, change "lever" to --- liver ---.
Column 3, line 37, change "and" to --- ad ---.
Column 3, line 46, change "scalk" to --- scald ---.
Column 4, Table 1, under "Trace Elements", change "Mangenese" to --- Manganese ---.
Column 5, line 39, change "pearance" to --- pearing ---.
Column 5, line 54, change "$C_{18}$" to --- C18 ---.
Column 5, line 55, change "10u" to --- 10µ ---.
Column 5, line 56, change "Massi" to --- Mass. ---.
Column 6, line 35, change "al." to --- al.: ---.
Column 6, line 55, change "data" to --- Data ---.
Column 10, line 18, change "810 b" to --- 810 B ---.

Signed and Sealed this

Tenth Day of December 1985

[SEAL]

Attest:

DONALD J. QUIGG

Attesting Officer

Commissioner of Patents and Trademarks